United States Patent [19]
Van Cleef

[11] Patent Number: 5,792,155
[45] Date of Patent: Aug. 11, 1998

[54] PROCESS FOR PARTIALLY OR TOTALLY FLATTENING A VEIN

[76] Inventor: Jean-Francois Van Cleef, 45 rue de la chaussée d'Antin, Paris, France

[21] Appl. No.: 574,861

[22] Filed: Dec. 19, 1995

Related U.S. Application Data

[63] Continuation of Ser. No. 182,128, Jan. 13, 1994, abandoned.

[30] Foreign Application Priority Data

Jul. 16, 1991 [FR] France ............... 91 08935

[51] Int. Cl.⁶ .................................. A61B 17/12
[52] U.S. Cl. ........................... 606/158; 606/198
[58] Field of Search ................... 606/158, 200, 606/198, 157, 151; 128/831, 843

[56] References Cited

U.S. PATENT DOCUMENTS

| | | | |
|---|---|---|---|
| 1,123,290 | 1/1915 | von Herff | 606/158 X |
| 3,586,002 | 6/1971 | Wood | 606/221 |
| 3,716,058 | 2/1973 | Tanner | 606/221 |
| 4,586,503 | 5/1986 | Kirsch et al. | 606/151 X |
| 4,990,156 | 2/1991 | Lefebvre | 606/200 |
| 5,002,562 | 3/1991 | Oberlander | 606/221 |
| 5,026,390 | 6/1991 | Brown | 606/221 |
| 5,092,870 | 3/1992 | Matermeier | 606/151 |
| 5,171,252 | 12/1992 | Friedland | 606/151 |

FOREIGN PATENT DOCUMENTS

| | | | |
|---|---|---|---|
| 2608418 | 6/1988 | France | A61B 17/00 |
| 3203410 | 11/1982 | Germany | A61B 17/12 |

*Primary Examiner*—Michael H. Thaler
*Attorney, Agent, or Firm*—Ladas & Parry

[57] ABSTRACT

The intravenous device of the invention enables a vein to be partially or totally flattened. The device comprises at least two presser rods (1, 2) which are interconnected by means of at least one spreader element (3) having a spring effect, and each of said rods being suitable for bearing against a respective one of two opposite borders of a vein. Said device (4) is substantially planar when in position in a vein.

14 Claims, 2 Drawing Sheets

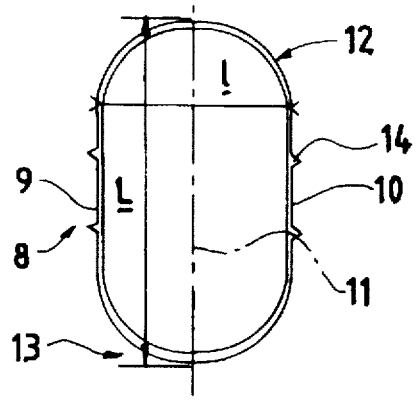
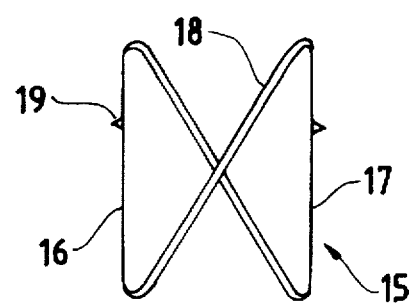
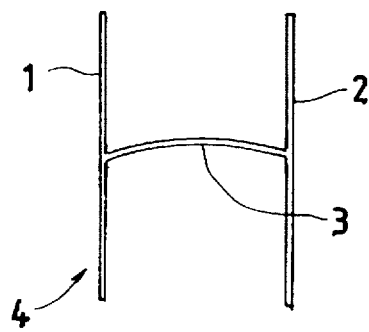
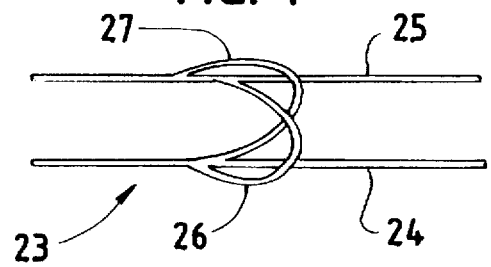
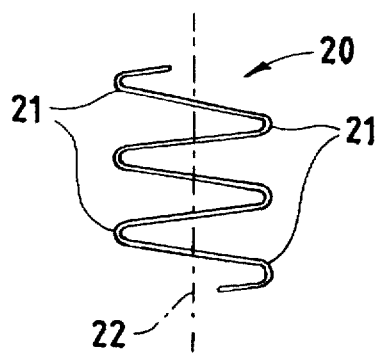
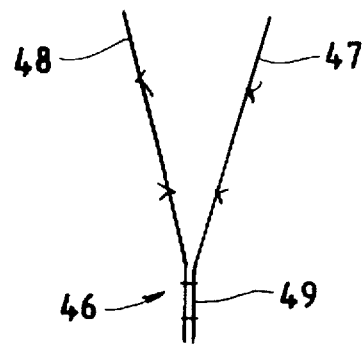

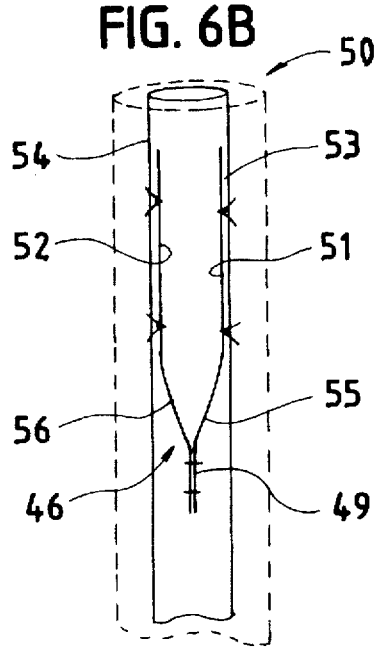
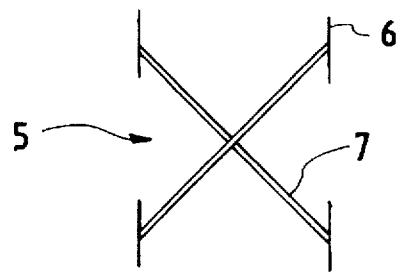
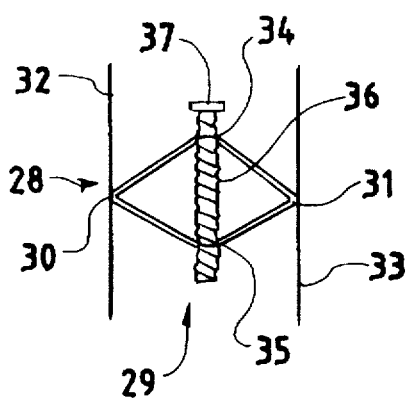
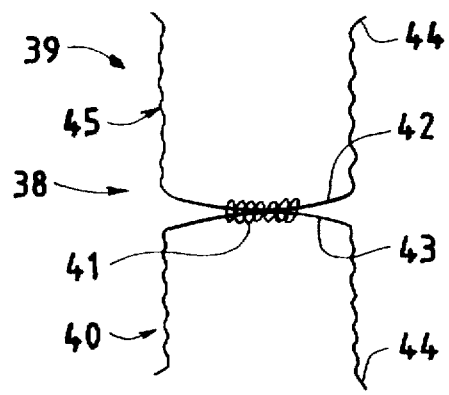

PROCESS FOR PARTIALLY OR TOTALLY FLATTENING A VEIN

This is a continuation of application Ser. No. 08/182,128, filed as PCT/FR92/00688 Jul. 16, 1992, published as WO93/01764 Feb. 4, 1993, now abandoned.

The present invention relates to an intravenous device, relating to the field of angiology and in particular to the treatment of varicose veins, said device enabling the lumen of the vein to be partially or totally flattened.

Traditionally, veins have been subjected to external ligatures by means of stitches or clips. Some doctors are of the opinion that placing springs on the outsides of the veins prevents such veins dilating and prevents the formation of varices. Others propose using mechanical valves, of the non-return type, at the sapheno-femural junction.

Known intravenous devices include filter type devices for the vena cava or cylindrical endoprostheses which are intended to maintain or reinforce the opening of the venous lumen for grafts or shunts, i.e. bypasses putting the arterial circuit into communication with the venous circuit.

Proposals have already been made in document FR 2 652 737 for a filter that is designed to be installed in the inferior vena cava to retain therein clots that could give rise to pulmonary embolism. That filter is made from a remanent spring shaped in the form of a spiral having three non-touching turns with the middle turn being of larger diameter than the other two. That filter gives rise to a certain amount of flattening in the vena cava in which it is installed, while its shape comprising three non-touching turns prevents any significant obstruction of the lumen of the vein, with blood flow merely being split into six semicircular segments.

When the lumen of the vein is to be genuinely obstructed, present practice is to use voluminous objects such as balloons or cylinders which can be felt through the skin and which run the risk of migrating and of giving rise to highly inflammatory thrombosis. The object sought by the Applicant is to propose an intravenous device that mitigates the drawbacks of the devices mentioned above in that it makes it possible to obstruct the lumen of a vein partially or completely without any risk of migration or of thrombosis.

This object is completely achieved by the intravenous device of the invention. It comprises a device for partially or totally flattening the lumen of a vein, which device is substantially plane and includes at least two presser rods, said rods being connected together by at least one spring-forming spreader element and being suitable for bearing respectively against opposite borders of a vein.

The Applicant has taken advantage of the observation that a vein, which is a collapsible tube, has a preferred flattening plane which, in the case of a superficial vein for example, is parallel to the surface of the skin. Recently, venous endoscopy has made it possible to define four component elements of a vein, for example the saphenous vein, namely an inner or deep "wallside" or face, an outer or superficial face, and two borders uniting the two faces. Below in the present application, the term "border of a vein" is used to designate one or other of said two elements.

At a valve, the borders of the vein are in the form of commissures, constituted by the union of the cusps.

Valvular clearance and speed of blood circulation are improved by ovalizing the lumen of the vein.

Thus, when the intravenous device of the invention is placed inside a vein, it substantially occupies a plane which, if the vein is a superficial plane, is parallel to the skin, i.e. it complies with the axis of preferred flattening of the vein. The spreader element causes it to urge the two borders of the vein away from each other, and consequently tends to move the inner and outer faces of the vein towards each other.

It will be understood that the thrust area corresponding to the zone of contact between the presser rods and the inside wall of the vein must be large enough to avoid any risk of tearing and perforation, given the fragility of venous tissue.

All sorts of spring effect spreader elements may be used, providing they are capable of lying substantially in a plane between the presser rods when the device has been put into place in a vein.

In one embodiment, the spreader element is X-shaped and comprises four presser rods disposed at the four ends of said element.

In another embodiment, the spreader element includes portions, preferably flattened portions, suitable for acting as presser rods. Naturally, in this case, the portions suitable for acting as presser rods must be substantially rectilinear. For example, the device may have the form of an elongated ellipse and the two presser rods may be constituted by the facing portions that are substantially parallel to the major axis.

In another example, the spreader element consists in a sinusoidal spring wire having flattened vertices forming the presser rods.

In another example, the spreader element consists in a V-shape spring with the free ends of the branches of the V-shape acting as presser rods.

Advantageously, the intravenous device of the invention includes anchor elements, in particular situated on all or part of the presser rods. These elements must enable the device to be locked in position relative to the inside wall of the vein and to prevent any migration of the device.

Advantageously, the presser rods are slightly corrugated so as to increase their area of contact with the wall of the vein, and thus increase their anchoring capacity.

When the presser rods and the spreader element are independent from each other, the spreader element is fixed to the presser rods by welding or by means of joints, e.g. of the hinge type.

Advantageously, the intravenous device of the invention is fitted with adjustment means, serving firstly to enable it to be adapted to the inside diameter of a vein, and secondly enabling the desired degree of flattening of the vein to be determined. Given these adjustment means, it is possible to use a single device either to partially flatten or ovalize a vein or else to completely flatten or obstruct the vein.

In a particular embodiment, the spreader element is in the form of a lozenge and the adjustment means are constituted by a worm screw or rack system placed along the longitudinal axis of the lozenge.

The intravenous device of the invention is substantially plane when it is in position inside a vein. Which is to be understood as meaning that it is accurately plane when the spreader element lies accurately in the same plane as the presser rods. Nevertheless, it is considered as being substantially plane providing all or a part of the spreader element lies at a small distance from the plane that is formed by the presser rods. In particular, this is obtained in the case of a device that is H-shaped having at least one curved crossbar situated above the plane formed by the presser rods. The H-shaped device preferably has two curved crossbars that curve in opposite directions, one being situated above and the other below the plane formed by the presser rods. Under such circumstances, the two crossbars delimit a substantially oval passage through which blood can flow inside the vein. This shape corresponds to the vein being partially flattened, with the two crossbars preventing the inner and outer faces of the vein coming together, and thus preventing the vein being completely obstructed.

This particular embodiment is preferably used when it is desired to fill the intercorneal space of the valves and to reinforce the tensioning arc function of the valvular thickening. Under such circumstances, the concave curvature of the crossbars is designed so as to fit closely to the shape of the two valvular thickenings.

Advantageously, at least one of the rods or the spreader element is made of a material suitable for containing and diffusing medicinal substances.

Advantageously, the intravenous device of the invention is made completely or in part of a material that is resorbable.

In a particular embodiment designed for sectioning or sclerosing the wall of the vein, the intravenous device is made up of two distinct assemblies, each assembly being constituted by at least two presser rods and by a spreader element; said assemblies are connected together by their spreader elements by means of a resorbable link; the four rods are provided with anchor means, and the resorbable link is impregnated with a substance suitable for chemically sclerosing or sectioning the wall of the vein. Thus, when the substance has been diffused and the link has been resorbed, the spreader elements are to be found on respective opposite borders of the section in the vein, thereby enabling the two portions thereof to be fully obstructed relative thereto.

The present invention will be better understood on reading the following description of various embodiments of an intravenous device for partially or totally flattening a vein, the device including presser rods and a spreader element substantially in the same plane, and being shown in the accompanying drawings, in which:

FIG. 1 is a view of a device in the form of an elongated ellipse;

FIG. 2 is a view of a device in the form of a cross having two presser rods;

FIG. 3 is a view of a device in the form of an H with a single crossbar lying in the same plane as the presser rods;

FIG. 4 is a view of an H-shaped device having two curved crossbars;

FIG. 5 is a view of a device that is sinusoidal in shape;

FIGS. 6A and 6B are two views of a device in which the spreader element is V-shaped, the device being shown in the relaxed state (FIG. 6A) and in place in a vein (FIG. 6B);

FIG. 7 is a view of an X-shaped device having four rods;

FIG. 8 is a view of a device whose spreader element is in the form of a lozenge provided with a device for adjusting spread; and FIG. 9 is a view of a device having two dissociable assemblies for obstructing a vein.

The intravenous device of the invention is intended to perform partial flattening, i.e. to improve ovalization of a vein when its ovalization is insufficient, or else to perform total flattening, i.e. to obstruct a vein.

It is known that the wall of a vein is not circumferentially uniform and that the capacity of the vein for being flattened is preferential in a determined plane, which plane is parallel to the surface of the skin when the vein is a superficial vein. Thus, a given vein wall can be defined as two faces united by two borders: an inner or deep face directed towards the inside of the body, an outer or superficial face directed towards the skin, and two borders uniting said two faces.

The device of the invention must be capable of being used to remedy or take action in the event of misfunction of the wall of a vein.

The means implemented in the device serve to move the two borders of the vein further apart to some extent, and consequently to move the inner and outer faces towards each other. Such movement towards each other can lead either to improved ovalization of the lumen of the vein, or else, optionally, to the two faces of the vein being moved all the way towards each other, thereby obstructing the lumen of the vein.

The means implemented consist in at least two presser rods 1 and 2 that are interconnected by a spreader element 3.

When the device 4 is placed inside a vein, each of the two presser rods 1 and 2 is intended to bear against a respective one of the two borders of the vein. The spring-forming spreader element must exert a certain pressure force on the two rods 1 and 2 so as to urge them apart from each other and press them against the two borders of the vein. Thus, when they are placed inside a vein, the two rods 1 and 2 are substantially parallel.

The device 4 shown in FIG. 3 is an example of a very simple embodiment in which the spreader element 3 is a metal wire. The device 4 is H-shaped, with the spreader element 3 constituting the crossbar of the Hshape and having a curved shape that occupies the same plane as the two rods 1 and 2.

Spreaders of other shapes may be envisaged, e.g. spreaders having the following shapes: Ω, horseshoe-shape, N, 7, T, cross-of-Lorraine, ladder, Y, Z, S, triangle, or oval.

In FIG. 7, there can be seen a device 5 which comprises four presser rods 6 of smaller size and fixed to respective ones of the four ends of the spreader element 7 which is X-shaped.

In all of the examples described above, the presser rods are assembled to the spreader element proper. Under such circumstances, the rods are fixed to the spreader element, in particular by welding or by joints, in particular joints of the hinge type.

In order to simplify physical embodiment of the device, it is naturally preferable for the device to be a single piece and to have no fixing points between its various elements. The three examples shown in FIGS. 1, 2, and 5 are single-piece embodiments of the device in which the presser rods are constituted by portions of the spreader element.

In FIG. 1, there can be seen a device 8 which consists in a metal ellipse of elongated shape, having a length L along the major axis 11 of the ellipse. This ellipse is remarkable in that parallel to the axis 11 it includes two substantially rectilinear portions 9 and 10 that act as presser rods. The device 8 thus includes two spreader elements 12 and 13 occupying the curved ends of the ellipse interconnecting the portions 9 and 10.

In a particular embodiment, the device 8 was made using a wire of chromium-cobalt in the ratio 40/60. The wire was circular in section having a diameter of 0.3 mm at its two curved ends 12 and 13 and flattened to be substantially in the form of a 4 mm wide tape in its two rectilinear portions 9 and 10 acting as presser rods. When in position in a vein, the device 8 of FIG. 1 had a length L of 3 cm and a width 1 of 8 mm. In addition, the portions 9 and 10 were provided with teeth 14 directed towards the outside of the ellipse so as to anchor the device 8 in the wall of the vein.

FIG. 2 shows a device 15 comprising two rods 16 and 17 interconnected by an X-shaped spreader element 18. Each of the rods 16 and 17 constitutes a rectilinear extension of two lateral ends of the X-shape. Each of the rods 16 and 17 is provided on its outside face (i.e. its face directed towards the outside of the X-shape), with an anchoring spike 19 placed substantially two-thirds of the way along the length of said rod.

FIG. 5 shows a device 20 in the form of a sinusoid. The sinusoid is made using a metal wire. The eight vertices 21 on either border of the transverse axis 22 of the sinusoid are flattened and constitute presser rods of small size.

In all of the examples described above, the spreader element lies exactly in the same plane as the presser rods. Such versions are particularly suitable for obtaining either ovalization or obstruction of the lumen of a vein.

In the example shown in FIG. 4, the device 23 is suitable for ovalization only of the lumen of a vein and is not suitable for obstructing a vein. The device 23 is H-shaped, having two presser rods 24 and 25 interconnected by two crossbars 26 and 27. These two crossbars 26 and 27 are curved. As shown in FIG. 4, one of them, 27, is situated above the plane of the rods 24 and 25, whereas the other one, 26, lies beneath said plane. It will be understood that when the device is put into place inside a vein, and the rods 24 and 25 are pressed against the borders of the vein, then the two crossbars 26 and 27 form a spreader element that defines a through zone for the flow of blood and prevent the inner and outer faces of the wall of the vein from coming into contact with each other.

This particular version as shown in FIG. 4 is especially useful for performing valvular consolidation. Under such circumstances, the crossbars 26 and 27 are curved in such a manner that once the ends of the bars have been placed in the intercorneal space, they fit closely to the valvular thickenings. In this way, the action of the presser rods when pushed apart from each other by the spreader elements stretches the free borders of the valves and reinforces the tensioning arc function of the valvular thickenings.

The device 28 shown in FIG. 8 includes adjustment means enabling it to be adapted to the geometry of the vein lumen or serving to determine the desired degree of vein flattening. Said adjustment means are constituted by a spreader element 29 in the form of a lozenge having two opposite vertices 30 and 31 fixed to two presser rods 32 and 33, and having its other two vertices 34 and 35 provided with tapped holes. A threaded rod 36 interconnects the two vertices 34 and 35 and is fitted at one of its ends with an adjustment screw 37. It is thus possible to use the adjustment screw 37 to vary the interior angle of the lozenge and thus to modulate the tension force directed towards the rods 32 and 33 by the spreader system 29.

The embodiment shown in FIG. 9 relates more specifically to sectioning or sclerosing a vein. This device 38 comprises two assemblies 39 and 40 that are interconnected by means of a link 41. Each of these two assemblies 39 and 40 is U-shaped and the two assemblies are connected together via their bases 42 and 43 which also act as spreader elements with the branches of the U-shapes acting as presser rods. Each of the branches is terminated by an outwardly-directed hook 44 enabling the device 38 to be anchored when it is put into place in a vein. The two bases 42 and 43 are united by resorbable catgut, impregnated with a substance for inducing sclerosis.

When the device 38 is put into place in a vein, diffusion of the sclerosis-producing substance sections the vein, while the two elements 39 and 40 anchored on either border of the sectioned zone ensure that the two ends of the sectioned vein remain in place. Naturally the extension force applied by the bases 42 and 43 is determined so as to achieve total flattening of the vein and thus obstruction thereof at the sectioned ends.

In the embodiment shown in FIG. 6A, the device 46 is V-shaped. It is constituted by two blades 47 and 48 that are secured against each other at the end 49, e.g. by welding. Each blade 47 and 48 acts both as a spreader element in a zone close to the common end 49, and as a presser rod towards its free end, as can be seen by examining FIG. 6B which shows the said device 46 in place inside a vein 50. The end portions 51 and 52 of the two blades 47 and 48 are pressed against the borders 53 and 54 of the vein 50 and they push them apart under the spring effect from the portions 55 and 56 close to the common end 49. These portions 55 and 56 are preferably paralleled by reinforcing blades.

The above embodiment is very flexible and insertion thereof into a vein is facilitated by the fact that the two blades can easily be folded together inside an insertion catheter.

The device of the invention is put into place in the same manner as is performed in the field of filters. It takes place through a trocar or through a cut-down vein (i.e. a vein that has been brought to the surface). A catheter carrying ducts, hoses, optionally with predetermined bending, and with or without a mandrel or with or without a guide wire is inserted into a vein until it reaches the location where the device is to be released. In order to dispose the device so that its general plane coincides with the direction of the two borders of the vein, the distal end of the catheter may be flattened or its inside surface may be grooved.

A pusher rod disposed inside the carrying catheter is used for pushing out the device and releasing it outside the catheter.

It will be understood that the distal end of the pusher rod must come into contact with the device in order to achieve such expulsion. In order to improve the orientation of the device while it is being released, the distal end of the pusher rod may advantageously be shaped so as to co-operate with the zone of the device that comes directly into contact with said rod in such a manner that rotation of the pusher rod causes corresponding rotation of the device. For example, the pusher rod may have a flattened lug at its end while the facing zone of the device may include a slot complementary to said lug. Thus, the distal end of the pusher rod can penetrate into the device and rotate it, after which it can be disconnected from the device merely by the rod being withdrawn.

Similarly, for the embodiment shown in FIG. 8, the end of the pusher rod may contribute, once the device has been put into place, to adjusting the spacing between the presser rods. This can be done merely by providing the adjustment screw 37 with a notch or slot in which the end of the pusher rod can be received.

Naturally, the device may be released in the same way as filters are released together with injections of sclerosis-producing, anticoagulant, or other medicaments. To facilitate such release, the catheter and the pusher rod may have visible marks at their proximal ends outside the patient, serving in particular to show the orientation of the device close to their distal ends inside said patient.

When the device includes anchor means, two push rods are used to avoid said anchor means rubbing along the inside surface of the carrying catheter.

The device of the invention may be made, completely or in part, from materials that enable medicinal substances to be diffused, e.g. anti-inflammatory substances, sclerosis-producing substances, vasoconstrictors, or other substances. A biological adhesive or resin may be used.

Such a device may also be implemented, completely or in part, by means of a resorbable material, such as catgut.

The invention is not limited to the embodiments described above by way of non-exhaustive example. In particular, it may be implemented either in the form of a single piece or it may be built up from a plurality of elements, each of which elements may be made of a different material, e.g. stainless steel, titanium, a polymer material, . . . . The materials used may have shape memory or they may also have been subjected to surface treatment in order to increase sclerosis reactions, for example by using copper, or on the contrary to increase biocompatibility, e.g. by means of heparin-containing fluorocarbons.

In its spreader element, the device of the invention may also include a ring or a hook for facilitating its release or its recovery. In addition, it may include means enabling it to be identified within the patient, e.g. radio-opaque components, components having a high echo-generating capacity, components that are colored to show up well in venous endoscopy, or components that conduct light for identification by cutaneous translumination. The device of the invention for providing partial or total flattening of a vein is advantageous in the treatment of varices, venous dilatation, angiomas, chronic deep venous insufficiency, valvular consolidation, and sclerosis, without that list being exhaustive.

I claim:

1. A process for partially or totally flattening a vein comprising:
    inserting into said vein at a predetermined situs a vein flattening device which comprises at least two presser rods interconnected by at least one spring-forming spreader element, said rods being substantially parallel, and said device being substantially planar when it is positioned in said vein;
    releasing the two presser rods of the flattening device which is so positioned in the vein such that each of said presser rods bears against a respective one of the two opposite borders of the vein, thereby moving said borders apart.

2. The process of claim 1 wherein the flattening device comprises adjustment means for adjusting the spacing between the presser rods, and the process further comprises, prior to the insertion in the vein, adjusting the distance between the presser rods, firstly to adapt the flattening device to the inside diameter of the vein, and secondly to determine the desired degree of flattening of the vein.

3. The process of claim 2 wherein the spreader element is in the form of a lozenge, and the adjustment means consist in a worm screw or rack system extending along the longitudinal axis.

4. The process of claim 1 wherein the vein flattening device is in the form of an elongated ellipse, and in that the two presser rods are constituted by the facing portions of the ellipse that are substantially parallel to the major axis.

5. The process of claim 1 wherein the vein flattening device is substantially V-shaped and contains two blades secured one against the other at the apex of the V, each blade acting as a presser rod.

6. The process of claim 1 wherein all or a portion of the presser rods of the vein flattening device are fitted with anchor elements.

7. The process of claim 1 wherein each presser rod includes corrugations.

8. The process of claim 1 wherein the vein flattening device includes an adjustment means for adjusting the spacing between the presser rods.

9. The process of claim 1 wherein the spreader element is in the form of a lozenge, the adjustment means consisting in a worm screw or rack system extending along the longitudinal axis of the lozenge.

10. The process of claim 1 wherein the vein flattening device is H-shaped, having one or two crossbars and in that the bar(s) of said H-shape constituting the spreader element are curved and do not lie in the plane of the presser rods.

11. The process of claim 10 wherein the vein flattening device is designed for placement at a valve, the crossbar(s) being concave and suitable for fitting closely to the shape of one or both valvular thickenings.

12. The process of claim 1 wherein at least one of the rods or the spreader elements is made of a material suitable for containing and diffusing medicinal substances.

13. The process of claim 1 wherein the vein flattening device is at least partially resorbable.

14. The process of claim 1 wherein the vein flattening device is made up of two distinct assemblies, each assembly comprising at least two rods and a spreader element, said assemblies having their spreader elements connected together by means of a resorbable link wherein four rods are provided with respective anchoring means in that the resorbable link is impregnated with a substance suitable for chemically sclerosing or sectioning the wall of a vein.

* * * * *